(12) United States Patent
Jackson

(10) Patent No.: US 7,658,744 B2
(45) Date of Patent: Feb. 9, 2010

(54) MULTIPLE BALLOON CATHETER

(75) Inventor: Brad Jackson, San Diego, CA (US)

(73) Assignee: Boston Scientific Scimed, Inc., Maple Grove, IN (US)

( * ) Notice: Subject to any disclaimer, the term of this patent is extended or adjusted under 35 U.S.C. 154(b) by 592 days.

(21) Appl. No.: 11/003,945

(22) Filed: Dec. 3, 2004

(65) Prior Publication Data

US 2006/0129093 A1    Jun. 15, 2006

(51) Int. Cl.
 *A61B 17/22* (2006.01)
(52) U.S. Cl. .................... 606/159; 606/194
(58) Field of Classification Search ............ 604/101.01, 604/95.03, 96.01, 509, 101.02, 101.03, 101.04, 604/101.05, 103, 103.07, 912, 917, 919, 604/267, 268; 606/194, 192, 159, 170
See application file for complete search history.

(56) References Cited

U.S. PATENT DOCUMENTS

| | | | |
|---|---|---|---|
| 4,037,599 A | 7/1977 | Raulerson | 128/214.4 |
| 4,072,146 A | 2/1978 | Howes | 128/2.05 D |
| 4,493,696 A | 1/1985 | Uldall | 604/43 |
| 4,983,167 A | 1/1991 | Sahota | 606/194 |
| 5,019,042 A * | 5/1991 | Sahota | 604/101.01 |
| 5,053,004 A | 10/1991 | Markel et al. | 604/43 |
| 5,167,623 A | 12/1992 | Cianci et al. | 604/43 |
| 5,176,693 A | 1/1993 | Pannek, Jr. | 606/159 |
| 5,181,920 A | 1/1993 | Mueller et al. | 606/159 |
| 5,196,024 A * | 3/1993 | Barath | 606/159 |
| 5,207,648 A | 5/1993 | Gross | 604/164 |
| 5,221,255 A | 6/1993 | Mahurkar et al. | 604/43 |
| 5,221,256 A | 6/1993 | Mahurkar | 604/43 |
| 5,320,634 A | 6/1994 | Vigil et al. | 606/159 |
| 5,336,234 A * | 8/1994 | Vigil et al. | 606/159 |
| 5,395,311 A | 3/1995 | Andrews | 604/22 |
| 5,409,495 A | 4/1995 | Osborn | 606/108 |
| 5,423,745 A * | 6/1995 | Todd et al. | 604/500 |
| 5,616,149 A | 4/1997 | Barath | 606/159 |
| 5,620,457 A | 4/1997 | Pinchasik et al. | 606/194 |
| 5,628,746 A | 5/1997 | Clayman | 606/45 |
| 5,649,941 A | 7/1997 | Lary | 606/159 |
| 5,697,944 A | 12/1997 | Lary | 606/159 |
| 5,718,876 A | 2/1998 | Parekh et al. | 423/462 |
| 5,728,123 A * | 3/1998 | Lemelson et al. | 604/22 |
| 5,792,158 A | 8/1998 | Lary | 606/159 |
| 5,797,935 A * | 8/1998 | Barath | 606/159 |

(Continued)

FOREIGN PATENT DOCUMENTS

WO    2005/023153 A2    3/2005

OTHER PUBLICATIONS

U.S. Appl. No. 10/879,894, filed Jun. 23, 2004, Kunis.

*Primary Examiner*—Nicolas D Lucchesi
*Assistant Examiner*—Christopher D Koharski
(74) *Attorney, Agent, or Firm*—Crompton Seager & Tufte, LLC.

(57) ABSTRACT

A balloon catheter may be provided with multiple balloons. At least one of the balloons may include at least one blade. The multiple balloons may be inflated by a common inflation lumen, or by separate inflation lumens. In some embodiments, a predilation balloon may be provided to predilate a lesion prior to placement of a bladed balloon within the lesion.

1 Claim, 4 Drawing Sheets

U.S. PATENT DOCUMENTS

| | | | |
|---|---|---|---|
| 5,800,393 A * | 9/1998 | Sahota | 604/103.07 |
| 5,800,450 A | 9/1998 | Lary | 606/180 |
| 5,879,499 A | 3/1999 | Corvi | 156/175 |
| 5,951,514 A | 9/1999 | Sahota | 604/96 |
| 6,258,019 B1 * | 7/2001 | Verin et al. | 600/1 |
| 6,258,108 B1 | 7/2001 | Lary | 606/159 |
| 6,632,231 B2 * | 10/2003 | Radisch, Jr. | 606/159 |
| 6,776,771 B2 * | 8/2004 | van Moorlegem et al. | 604/101.01 |
| 7,066,905 B2 * | 6/2006 | Squire et al. | 604/103.08 |
| 2003/0040770 A1 | 2/2003 | Radisch, Jr. | 606/194 |
| 2003/0163082 A1 | 8/2003 | Mertens | 604/43 |
| 2004/0092870 A1 | 5/2004 | Squire et al. | |
| 2004/0243156 A1 | 12/2004 | Wu et al. | 606/159 |
| 2005/0038383 A1 * | 2/2005 | Kelley et al. | 604/103.06 |

\* cited by examiner

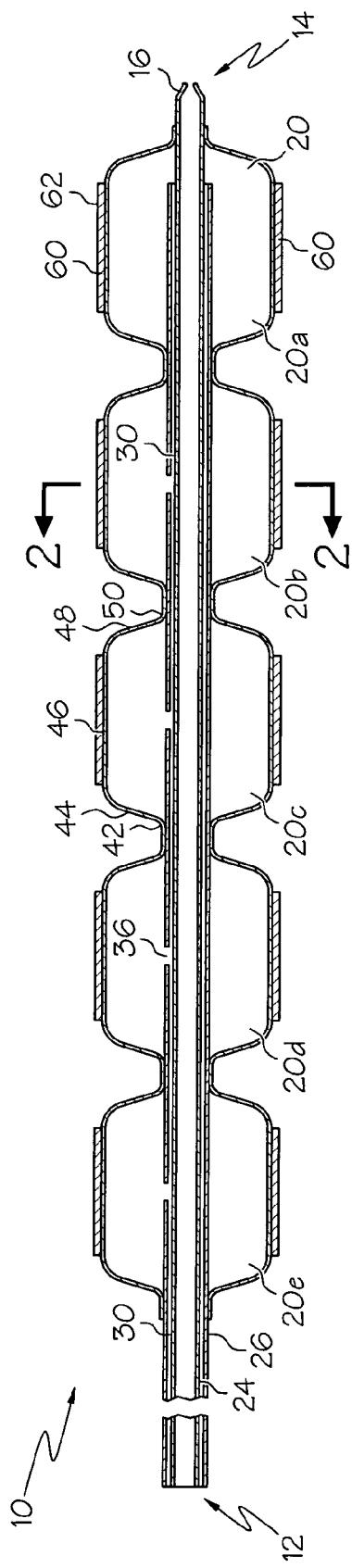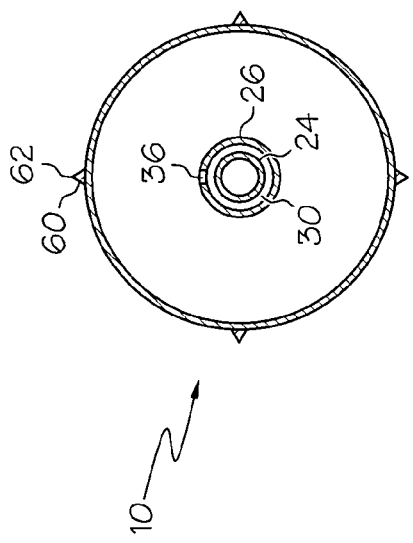

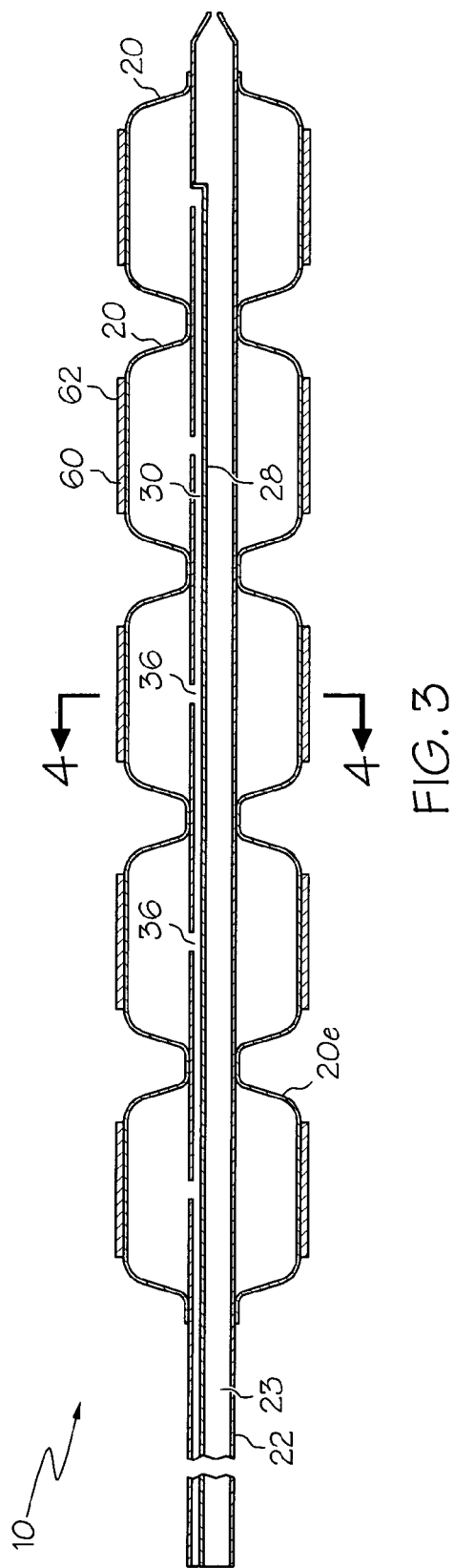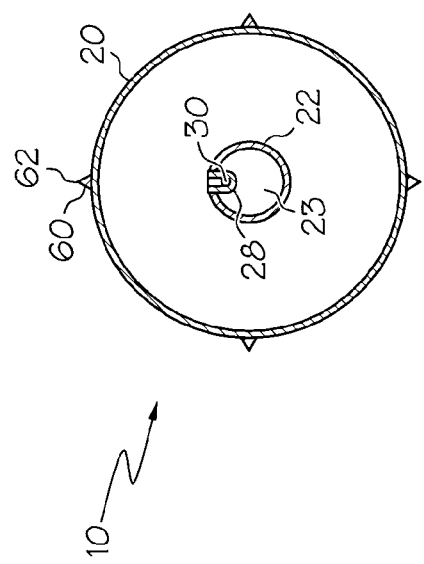

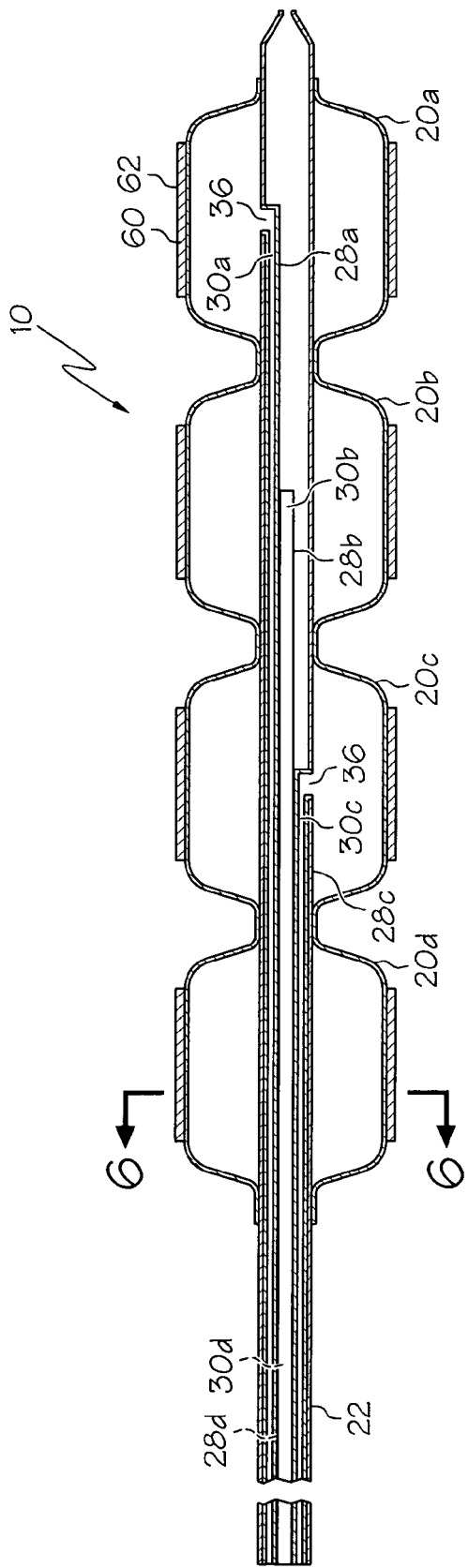
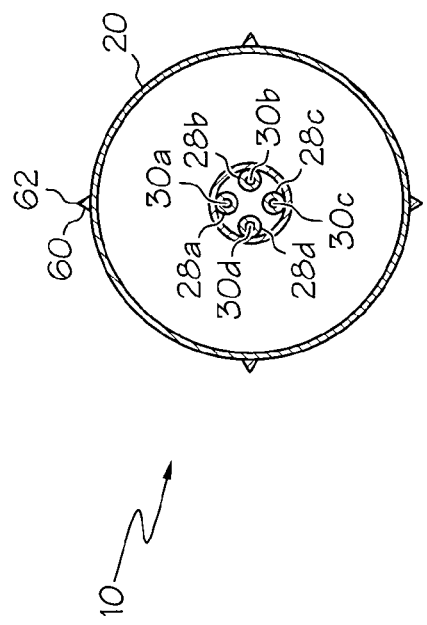

MULTIPLE BALLOON CATHETER

BACKGROUND OF THE INVENTION

This invention relates generally to balloon catheters, which are known in the art, and more specifically to balloon catheters which may be provided with cutting blades.

Percutaneous transluminal coronary angioplasty (PTCA) is a procedure which is well established for the treatment of blockages in the coronary and peripheral arteries.

The most widely used form of percutaneous angioplasty makes use of a dilatation balloon catheter. The provision of cutting blades upon the balloon catheter facilitates cutting and dilation of stenoses. An example of a balloon catheter with a cutting edge is disclosed in U.S. Pat. No. 5,616,149, the entire disclosure of which is incorporated herein by reference in its entirety.

The length of a balloon which includes blades may be limited because the blades are often more rigid than the balloon and/or catheter and therefore not as flexible in bending. A long balloon which has blades may be more difficult to maneuver through a tortuous anatomy than a nonbladed balloon or a shorter bladed balloon. When treating a fairly long region of stenosis using a bladed balloon, the balloon may be required to be deflated, repositioned and reinflated multiple times. It would be desirable to have a bladed balloon catheter capable of treating long areas of stenosis with minimal repositioning. Further, a catheter having a long balloon will generally straighten along its length when inflated. It would be desirable for a bladed balloon catheter to substantially follow vessel contour when inflated. It would further be desirable for a bladed balloon catheter to follow vessel contour when deflated to aid in traversing a tortuous anatomy and positioning the balloon at a lesion site.

Bladed balloons generally have a larger uninflated diameter than an equivalently sized nonbladed balloon. In some cases of stenosis, it may be more difficult to position a bladed balloon within the stenosis prior to inflation than an equivalently sized nonbladed balloon. In some cases, a bladed balloon in an uninflated state may be too large to fit into an area of stenosis, thus requiring a nonbladed balloon to be used. It would be desirable to provide a mechanism to predilate a lesion a predetermined amount immediately prior to the positioning of a bladed balloon within the lesion.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, a balloon catheter may comprise a catheter shaft having an inflation lumen extending therethrough, a first inflatable balloon having at least one blade and a second inflatable balloon. An interior portion of the first inflatable balloon and the second inflatable balloon may be in fluid communication with the inflation lumen.

In another embodiment, a balloon catheter may comprise a catheter shaft having a first inflation lumen and a second inflation lumen extending therethrough, a first inflatable balloon and a second inflatable balloon, at least one of said first and second balloons having at least one blade. An interior portion of the first inflatable balloon may be in fluid communication with the first inflation lumen and an interior portion of the second inflatable balloon may be in fluid communication with the second inflation lumen. In some embodiments the first balloon may comprise a predilation balloon, which may have an expanded diameter that is slightly larger than an unexpanded diameter of the second balloon.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

FIG. 1 shows a longitudinal cross-sectional side view of an embodiment of a multiple balloon catheter.

FIG. 2 shows a cross-sectional axial view of the embodiment of FIG. 1 taken along line 2-2 of FIG. 1.

FIG. 3 shows a longitudinal cross-sectional side view of another embodiment of a multiple balloon catheter.

FIG. 4 shows a cross-sectional axial view of the embodiment of FIG. 3 taken along line 4-4 of FIG. 3.

FIG. 5 shows a longitudinal cross-sectional side view of another embodiment of a multiple balloon catheter.

FIG. 6 shows a cross-sectional axial view of the embodiment of FIG. 3 taken along line 6-6 of FIG. 5.

DETAILED DESCRIPTION OF THE INVENTION

Figure 7:
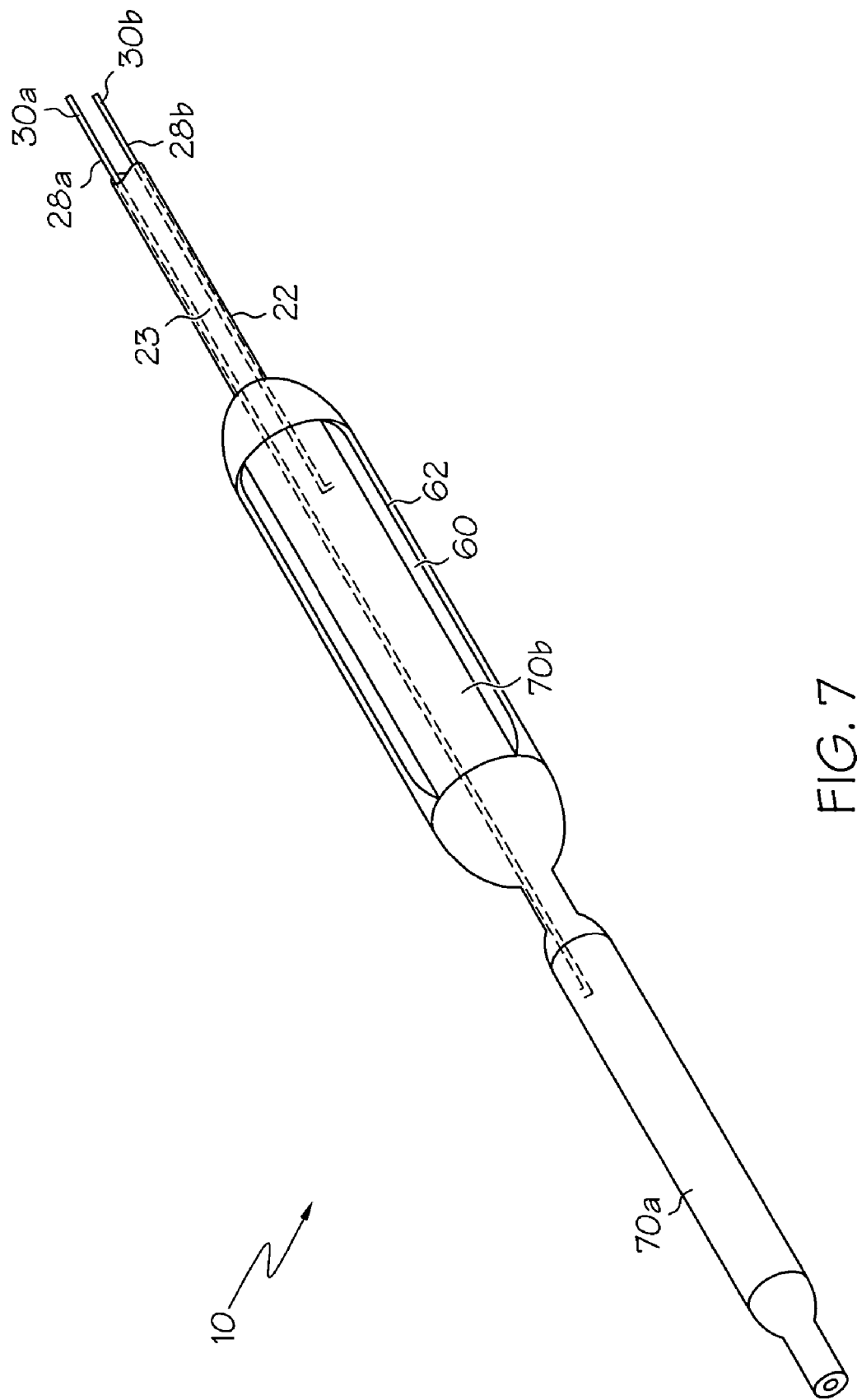
FIG. 7 depicts another embodiment of a multiple balloon catheter.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIGS. 1 and 2 show an embodiment of a balloon catheter 10 having multiple balloons 20, including a first balloon 20a and a second balloon 20b. The balloon catheter 10 may include any number of balloons 20. As depicted, the balloon catheter 20 further includes a third balloon 20c, a fourth balloon 20d and a fifth balloon 20e.

In order to accommodate a variety of vessel or lumen shapes and configurations, the various balloons 20 may be of similar or dissimilar sizes, lengths, diameters, shapes, etc.

The catheter 10 may include an inner shaft 24, an outer shaft 26, a proximal end 12, a distal end 14 and a tip 16. An inflation lumen 30 may be defined between the inner shaft 24 and the outer shaft 26. The inflation lumen 30 may be in fluid communication with an interior portion of each balloon 20, and may be used to inflate and/or deflate each balloon 20.

Generally, any suitable known catheter arrangement may be used with any suitable known balloon configuration to produce various embodiments of the invention.

In some embodiments, each balloon 20 may include a proximal waist portion 42, a proximal cone portion 44, a body portion 46, a distal cone portion 48 and a distal waist portion 50. In at least one embodiment, the distal waist portion 50 of the first balloon 20a may be secured to the inner shaft 24, and the proximal waist portion 42 of the first balloon 20a may be secured to the outer shaft 26. The distal waist portion 50 of the second balloon 20b and any subsequent balloons 20 may be secured to the outer shaft 26, and the proximal waist portion 42 of the first balloon 20a and any subsequent balloons 20 may be secured to the outer shaft 26.

Any or all of the balloons 20 may further include one or more blades 60. Each blade 60 may include a sharp cutting edge 62. In some embodiments, one or more balloons 20 do not include blades 60, whereas one or more other balloons 20 do include blades 60.

A blade 60 may be made from any suitable material, such as a metal, a polymer, a composite, a ceramic or any suitable combination thereof. In at least one embodiment, a blade 60 may be at least partially constructed of a shape memory material, such as nitinol and/or a shape memory polymer.

A blade 60 may have any suitable shape and orientation on the balloon 20, such as parallel to the longitudinal axis of the balloon 20 or oriented at an angle to the longitudinal axis of the balloon 20. In some embodiments, a blade 60 may span the length of the body portion 46 of a balloon 20. In some embodiments, a blade 60 may be segmented along its length. In some embodiments, blades 60 may spiral helically around a portion of the balloon 10 such as described in U.S. patent application Ser. No. 10/879,894, the entire disclosure of which is incorporated herein by reference.

Multiple blades 60 included on a common balloon 20 may have similar shapes and orientations or dissimilar shapes and orientations. Blades 60 of one balloon 20 may be shaped and oriented similarly or dissimilarly from blades 60 which are provided on another balloon 20 of the balloon catheter 10.

Blades 60 may be secured to a balloon 20 using any suitable method. In some embodiments, after a balloon 20 has been formed such as by extrusion, molding, or the like, one or more blades 60 may be engaged to the exterior surface of the balloon 20 using any suitable engagement method. For example, a blade 60 may by engaged to the balloon 20 by welding (e.g. laser welding, chemically welding, etc) and/or by mechanical engagement between the blade 60 and the balloon 20, such as by providing the blade 60 and the exterior surface of the balloon 20 with one or more interlocking surface features for mutual securement. In at least one embodiment, a chemical adhesive may be applied to one or both of the balloon 20 and the blade 60 to adhesively engage the blade 60 to the balloon 20.

In some embodiments, a blade 60 may be imbedded in a substrate material, such as a polyurethane pad, and the substrate may be secured to the balloon 20 as disclosed in U.S. Pat. No. 5,320,634, the entire disclosure of which is incorporated herein by reference in its entirety.

The outer shaft 26 of the catheter 10 may include one or more apertures 36 extending through the wall portion of the outer shaft 26. Each aperture 36 may be arranged to allow fluid communication between the inflation lumen 30 and a balloon 20. Thus, in some embodiments, a single inflation lumen 30 may be in fluid communication with all of the balloons 20 of the catheter 10, and all of the balloons 20 may be inflated and/or deflated simultaneously.

The multiple balloon catheter 10 may be used to dilate a long lesion which may span the length of a plurality of balloons 20. In some embodiments, the length of the balloons 20, the size of the blades 60 and the spacing between adjacent balloons 20 may be selected such that a long lesion may be treated with only one repositioning and re-inflation of the multiple balloon catheter 10.

The catheter 10 may be placed within a long lesion and the multiple balloons 20 may be inflated to dilate multiple portions of the lesion. The balloons 20 may then be deflated, and the catheter 10 may be repositioned such that the balloons 20 are positioned to dilate any undilated portions of the lesion. The balloons 20 may be re-inflated, thereby dilating the entire long lesion with only one repositioning and re-inflation.

FIGS. 3 and 4 show another embodiment of a balloon catheter 10. The catheter 10 may include any number of balloons 20. Each balloon 20 may include any number of blades 60.

The catheter 10 may include a main shaft 22 having an inner lumen 23. An inflation shaft 28 having an inflation lumen 30 may be disposed within the inner lumen 23. The main shaft 22 may include one or more apertures 36 extending through the wall portion of the main shaft 22. Each aperture 36 may be arranged to allow fluid communication between the inflation lumen 30 and a balloon 20. Thus, the inflation lumen 30 may be in fluid communication with all of the balloons 20 of the catheter 10, and all of the balloons 20 may be inflated and/or deflated simultaneously.

FIGS. 5 and 6 show another embodiment of a balloon catheter 10 including a first balloon 20a, a second balloon 20b, a third balloon 20c and a fourth balloon 20d. Each balloon 20 may be provided with at least one blade 60 having a cutting edge 62. Each balloon 20 may be individually inflatable and/or deflatable.

The catheter 10 may include a main shaft 22 having an inner lumen 23. A first inflation shaft 28a having a first inflation lumen 30a may be positioned within the inner lumen 23. The first inflation lumen 30a may be in fluid communication with an interior portion of the first balloon 20a via an aperture 36 through the wall of the main shaft 22. A second inflation shaft 28b having a second inflation lumen 30b may be positioned within the inner lumen 23. The second inflation lumen 30b may be in fluid communication with an interior portion of the second balloon 20b via an aperture 36 through the wall of the main shaft 22. A third inflation shaft 28c having a third inflation lumen 30c may be positioned within the inner lumen 23. The third inflation lumen 30c may be in fluid communication with an interior portion of the third balloon 20c via an aperture 36 through the wall of the main shaft 22. A fourth inflation shaft 28d having a fourth inflation lumen 30d may be positioned within the inner lumen 23. The fourth inflation lumen 30d may be in fluid communication with an interior portion of the fourth balloon 20d via an aperture 36 through the wall of the main shaft 22. Although FIGS. 5 and 6 show a catheter 10 having four balloons 20 and four respective inflation shafts 28, any suitable number of balloons and inflation shafts may be provided.

The catheter 10 may be used to dilate a long lesion. Each balloon 20 may be inflated and/or deflated individually as desired. For example, a catheter 10 having four separately inflatable balloons 20 may be used to treat a long lesion that spans the length of the four balloons 20. The catheter 10 may be positioned such that the ends of the first balloon 20a and the fourth balloon 20d are substantially aligned with the ends of the lesion. All of the balloons 20 may be inflated, thereby dilating four regions of the lesion while leaving three lesion peaks remaining between the four dilated regions. The balloons 20 may be deflated, and the catheter 10 may be repositioned such that the first, second and third balloons 20a, 20b, 20c are positioned to dilate the remaining peaks, and the fourth balloon 20d is not within the lesion. The first, second and third balloons 20a, 20b, 20c may be individually reinflated to dilate the remaining peaks, thereby completing treatment by fully dilating the entire lesion. The fourth balloon 20d, while not positioned within the lesion, need not be inflated.

Multiple lumen catheters are discussed in published U.S. Patent Application No. US-2003-0163082-A1, the entire disclosure of which is incorporated herein by reference in its entirety. Some further examples multiple lumen catheters may be found in U.S. Pat. Nos. 4,037,599; 4,072,146; 4,493,696; 5,053,004; 5,167,623; 5,207,648; 5,221,255; 5,221,256; 5,718,876 and 5,879,499; all of which are incorporated herein by reference.

FIG. 7 shows another embodiment of a balloon catheter 10 which may include a shaft 22 having an inner lumen 23, a first balloon 70a and a second balloon 70b. In some embodiments, the first balloon 70a is inflatable and/or deflatable independently from the second balloon 70b. A first inflation shaft 28a having a first inflation lumen 30a may be positioned within the inner lumen 23. The first inflation lumen 30a may be in fluid communication with an interior portion of the first balloon 70a via an aperture through the wall of the shaft 22. A second inflation shaft 28b having a second inflation lumen 30b may be positioned within the inner lumen 23. The second inflation lumen 30b may be in fluid communication with an interior portion of the second balloon 20b via an aperture through the wall of the shaft 22.

In some embodiments, the second balloon 70b may include at least one blade 60 having a cutting edge 62.

The first balloon 70a may comprise a predilation balloon which may be used to predilate a lesion. For example, some lesions sufficiently constrict a vessel such that a bladed balloon is too large to be placed within the lesion, while a smaller, nonbladed balloon is able to cross the lesion. A predilation balloon 70a may be placed within the lesion and inflated, thereby predilating the lesion a predetermined amount and allowing the bladed balloon to be properly positioned within the lesion and inflated.

In some embodiments, a predilation balloon 70a may be a non-bladed balloon and may have a diameter that is as small as possible while allowing sufficient predilation of a lesion to allow a subsequent balloon to traverse the lesion. In some embodiments, the unexpanded diameter of the predilation balloon 70a is less than the unexpanded diameter of the second balloon 70b. In some embodiments, the expanded diameter of the predilation balloon 70a is less than the expanded diameter of the second balloon 70b. In some embodiments, the expanded diameter of a predilation balloon 70a may be the same or slightly greater than the unexpanded diameter of the second balloon 70b.

While FIG. 7 shows a catheter having first and second inflation shafts, any suitable multiple lumen catheter may be used.

Various embodiments of a balloon catheter 10 may include any number of balloons. Each balloon may include any number of blades.

In embodiments where multiple inflation lumens are desirable, any suitable embodiment of a multi-lumen catheter may be used.

A catheter having any desirable number of inflation lumens may be used to form a balloon catheter. Any desirable number of balloons may be provided on the balloon catheter, and the various balloons may be arranged to be inflated by the various inflation lumens in any desired configuration.

Any embodiment of a balloon catheter 10 may include a predilation balloon as discussed herein with respect to FIG. 7. In some embodiments, a predilation balloon may be separately inflatable from the other balloons using a separate inflation lumen.

A balloon 20 may be made of any suitable balloon material including, for example, compliant and non-compliant materials and combinations thereof. Some examples of suitable materials for constructing the balloon body 18 include but are not limited to: low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyetherpolyamide copolymers; copolymer polyolefin material available from E.I. DuPont de Nemours and Co. (Wilmington, Del.), under the trade name SurlynJ; ionomer and a polyether block amide available under the trade name PEBAX; high pressure polymeric materials, such as thermoplastic polymers and thermoset polymeric materials, poly(ethylene terephthalate) (commonly referred to as PET), polyimide, thermoplastic polyamide, polyamides, polyesters, polycarbonates, polyphenylene sulfides, polypropylene and rigid polyurethane; one or more liquid crystal polymers; and combinations of one or more of any of the above, as well as others.

In some embodiments the balloon catheter 10 may be configured to deliver one or more therapeutic agents to a stenosis, aneurysm or lesion within a body lumen. In some embodiments at least a portion of a blade 60 may be configured to include one or more holes, notches, or other surface features to which one or more therapeutic agents may be placed for delivery to the aneurysm site. A therapeutic agent may be placed on the blade(s) 60 and/or the exterior surface of a balloon 20 in the form of one or more coatings. In at least one embodiment the coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The present invention also relates to methods of using the balloon catheters described herein.

A method of treating a vascular occlusion may comprise providing a catheter having a first inflation balloon and a second inflation balloon. The second inflation balloon may include at least one blade. The catheter may be positioned with the first inflation balloon oriented within a vascular occlusion, and the first inflation balloon may be inflated to predilate the vascular occlusion. The catheter may then be positioned with the second inflation balloon oriented within the predilated vascular occlusion, and the second inflation balloon may be inflated to fully dilate the predilated vascular occlusion.

Another method of treating a lesion or vascular occlusion may comprise providing a catheter having a first inflation balloon and a second inflation balloon. The first inflation balloon may have a smaller inflated diameter than the second inflation balloon, and the second inflation balloon may include at least one blade. The first inflation balloon may also have a smaller uninflated diameter than the second inflation balloon. The catheter may be used to dilate a lesion which has restricted the opening of a vascular lumen to a size or diameter that less than an uninflated diameter of the second balloon. The catheter may be positioned with the first inflation balloon oriented within the lesion, and the first inflation balloon may be inflated to predilate the lesion such that the opening of the vascular lumen at the lesion site is equal to or larger than the uninflated diameter of the second inflation balloon. The first inflation balloon may be at least partially deflated. The catheter may then be positioned with the second inflation balloon oriented within the predilated lesion, and the second inflation balloon may be inflated to fully dilate the lesion. The second inflation balloon may be at least partially deflated, and the catheter may be removed.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A balloon catheter comprising:
- a catheter shaft having a longitudinal axis, the catheter shaft comprising an inner shaft and an outer shaft, an inflation lumen located between the inner shaft and the outer shaft;
- a first inflatable balloon comprising a first blade, the first inflatable balloon in fluid communication with the inflation lumen, a distal end of the first inflatable balloon attached to said inner shaft, a proximal end of the first inflatable balloon attached to said outer shaft; and
- a second inflatable balloon comprising a second blade, the second inflatable balloon in fluid communication with the inflation lumen;
- the first blade separated from the second blade by a first distance as measured in a direction parallel to the longitudinal axis, the first distance being less than a length of the first blade;
- wherein a distal end of the second inflatable balloon is attached to said outer shaft, and a proximal end of the second inflatable balloon is attached to said outer shaft.

* * * * *

UNITED STATES PATENT AND TRADEMARK OFFICE
CERTIFICATE OF CORRECTION

PATENT NO. : 7,658,744 B2  Page 1 of 1
APPLICATION NO. : 11/003945
DATED : February 9, 2010
INVENTOR(S) : Brad Jackson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this

Thirtieth Day of November, 2010

David J. Kappos
*Director of the United States Patent and Trademark Office*